United States Patent
Rizk

(10) Patent No.: US 9,084,733 B2
(45) Date of Patent: *Jul. 21, 2015

(54) CLEANSING COMPOSITION WITH CATIONIC SILANES AND SILICONES

(71) Applicant: L'OREAL, Paris (FR)

(72) Inventor: Kirolos Rizk, Helmetta, NJ (US)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 14/100,126

(22) Filed: Dec. 9, 2013

(65) Prior Publication Data

US 2015/0157545 A1    Jun. 11, 2015

(51) Int. Cl.

| | |
|---|---|
| *C11D 1/02* | (2006.01) |
| *C11D 1/90* | (2006.01) |
| *C11D 1/92* | (2006.01) |
| *C11D 9/36* | (2006.01) |
| *A61Q 5/02* | (2006.01) |
| *A61K 8/58* | (2006.01) |
| *A61K 8/42* | (2006.01) |
| *A61K 8/60* | (2006.01) |
| *A61K 8/898* | (2006.01) |
| *A61Q 5/12* | (2006.01) |

(52) U.S. Cl.
CPC . *A61K 8/585* (2013.01); *A61K 8/42* (2013.01); *A61K 8/602* (2013.01); *A61K 8/898* (2013.01); *A61Q 5/02* (2013.01); *A61Q 5/12* (2013.01)

(58) Field of Classification Search
CPC ............ C11D 1/02; C11D 1/662; C11D 1/90; C11D 1/92; C11D 9/36; A61Q 5/02
USPC ......... 510/119, 121, 123, 125, 127, 155, 426, 510/433, 466, 474, 490; 424/70.122, 70.19, 424/70.21, 70.24, 70.31
See application file for complete search history.

(56) References Cited

U.S. PATENT DOCUMENTS

| | | |
|---|---|---|
| 6,110,451 A | 8/2000 | Matz et al. |
| 2006/0135382 A1 | 6/2006 | Molenda |
| 2006/0217283 A1 | 9/2006 | De Salvert et al. |
| 2009/0041706 A1 | 2/2009 | Molenda et al. |
| 2009/0178210 A1* | 7/2009 | Bistram ............... 8/431 |
| 2011/0139170 A1* | 6/2011 | Hippe et al. ........ 132/202 |
| 2011/0150810 A1 | 6/2011 | Molenda et al. |
| 2011/0155163 A1 | 6/2011 | Viravau et al. |
| 2011/0155164 A1 | 6/2011 | Viravau et al. |
| 2012/0196783 A1 | 8/2012 | D'Aversa et al. |
| 2012/0251476 A1 | 10/2012 | Molenda et al. |
| 2013/0143784 A1 | 6/2013 | Rizk |

FOREIGN PATENT DOCUMENTS

| | | | |
|---|---|---|---|
| EP | 0095238 A2 | 11/1983 | |
| EP | 1504749 B1 | 12/2008 | |
| WO | WO-0048557 A1 | 8/2000 | |
| WO | 2010/069500 A1 | 6/2010 | |
| WO | WO 2012/175681 | * 12/2012 | ........ A61K 8/58 |

OTHER PUBLICATIONS

U.S. Appl. No. 14/100,117, filed Dec. 9, 2013, Kirolos Rizk.
U.S. Appl. No. 14/100,126, filed Dec. 9, 2013, Kirolos Rizk.
U.S. Appl. No. 14/100,144, filed Dec. 9, 2013, Kirolos Rizk.
U.S. Appl. No. 14/100,156, filed Dec. 9, 2013, Kirolos Rizk.
Jorg Kahre, Catherine Le Hen Ferrenbach, Laurence Robbe Tomine, Holger Tesmann, Tensio-Actifs Les alkylpolyglucosides une nouveaute en matiere de soin et de tolerance, Parfums Cosmetiques Actualites No. 131, Nov. 1996, pp. 49-61.
Notification of Transmittal of the International Search Report and the Written Opinion of the International Searching Authority, or the Declaration, as well as the Search Report and Written Opinion, International Application No. PCT/EP2014/077066, dated Mar. 9, 2015.

\* cited by examiner

*Primary Examiner* — Brian P Mruk
(74) *Attorney, Agent, or Firm* — Novak Druce Connolly Bove + Quigg LLP

(57) ABSTRACT

The present invention is directed to a cleansing composition containing:
(a) from about 6% to about 20% of at least one nonionic surfactant;
(b) from about 3% to about 10% of at least one amphoteric surfactant;
(c) from about 2% to about 8% of at least one anionic surfactant; and
(d) from about 0.01% to about 5% of at least one cationic silicone, cationic silane, cationic silane oligomer, or a mixture thereof;
wherein the amount of nonionic surfactant (a) present in the final composition is greater than the amount of the amphoteric surfactant (b), and the ratio of nonionic surfactant (a) to anionic surfactant (d) is at least 1.9:1; based on the weight percent of each surfactant in the final composition.

20 Claims, No Drawings

CLEANSING COMPOSITION WITH CATIONIC SILANES AND SILICONES

TECHNICAL FIELD

The present invention relates to personal cleansing compositions. More particularly, the invention relates to a shampoo composition having not only exceptional cleaning effect, but also improved conditioning properties.

BACKGROUND OF THE INVENTION

Conventional cleansing compositions such as shampoos, for example, contain standard surfactants such as anionic, nonionic and/or amphoteric type surfactants in amounts such that the anionic surfactant is typical present in the highest concentration of the foregoing three surfactants. This is because these anionic surfactants provide optimal foaming to the final composition. While nonionic surfactants are also often used in the cosmetic industry as they offer good cleansing, solubilizing and dispersing properties and are less irritating than anionic surfactants, their usage is typically limited to the secondary surfactant by percent in comparison to anionic surfactants due to their poor foaming ability as well as providing lower viscosity to the overall composition (i.e. the composition is thinner and more runny with increased amounts of the nonionic surfactant).

These cleaning compositions can be applied onto a wet keratinous substrate (e.g. hair or skin) and the lather they generate make it possible, after rinsing with water, to remove the diverse types of soils typically present on the hair or skin.

While these compositions provide good cleansing power, they often have poor intrinsic cosmetic properties due to the fact that the relatively aggressive nature of such a cleansing treatment may, in the long term, give rise to more or less pronounced damage on hair fibers or skin associated, for example, with the gradual removal of the fats or proteins contained in or at their surface. Thus, to improve the cosmetic properties of cleansing compositions, cationically modified silicone-based compounds are sometimes added to such compositions to act as conditioning agents and improve the tactile properties of said compositions. The amount of the cationically modified silicone-based compound(s) that can be used in these compositions, however, oftentimes is limited due to strong interaction and affinity of cationic compounds with anionic cleansing surfactants. This strong affinity and interaction between the cationically modified silicone-based compound and the anionic surfactants can lead to the formation of insoluble salts which causes phase separation resulting in unstable formulations. Furthermore the cationic compounds tent to negatively impact the foam quality of the compositions in terms of volume of foam generated as well as the sensorial feel of the foam. Additionally, the charge attraction between the cationically modified silicone-based compound(s) and the anionic surfactants tend to make it difficult to deposit the cationic silicone-based compound onto the hair fiber.

It is an object of the present invention to provide high foaming, effective cleaning compositions for use in personal care that also can provide increased conditioning effects, are stable and cost-effective.

BRIEF SUMMARY OF THE INVENTION

The present invention relates to an aqueous cleansing composition comprising:
(a) from about 6% to about 20% of at least one nonionic surfactant;
(b) from about 3% to about 10% of at least one amphoteric surfactant;
(c) from about 2% to about 8% of at least one anionic surfactant; and
(d) from about 0.01% to about 5% of at least one cationic silicone, cationic silane, cationic silane oligomer(s), or a mixture thereof;
wherein the amount of nonionic surfactant (a) present in the final composition is greater than the amount of the amphoteric surfactant (b); and wherein the ratio of nonionic surfactant (a) to anionic surfactant (c) is at least about 1.9:1, by weight, based on the weight percent of each surfactant in the final composition.

The present invention is also directed to a process for cleansing and conditioning a keratinous substrate involving contacting the keratinous substrate with the above-disclosed composition.

The present invention is also directed to a method of conditioning a keratinous substrate involving contacting the keratinous substrate with the above-disclosed composition.

The present invention is also directed to a method of increasing the deposition of hydrophobic non-ionic conditioning agents (such as silicones and oils) onto a keratinous substrate involving contacting the keratinous substrate with a non-ionic conditioning agent and the composition of the invention.

The present aqueous composition results from the finding that a blend of a specific amount and ratio of cleaning surfactants enables the composition additionally to incorporate at least one cationic silicone and/or silane or silane oligomers. The present composition provides not only good cleansing of keratinous substrates, but also affords foam having good volume and luxurious feel, while at the same time imparting increased conditioning properties onto the substrate all while reducing the amount of anionic surfactant. The composition is clear in appearance and highly viscous.

It is to be understood that both the foregoing general description and the following detailed description are exemplary and explanatory only, and are not restrictive of the invention.

DETAILED DESCRIPTION OF THE INVENTION

The present compositions provide not only good cleansing of keratinous substrates, but also create good and luxuriously feeling foam, while at the same time imparting increased conditioning properties onto the substrate all while reducing the amount of anionic surfactant. When used as shampoos, these compositions have foaming qualities at least comparable to, most often better than, traditional shampoos, even though they use nonionic surfactants as the primary surfactants and anionic surfactants only as tertiary surfactants. Also, because the compositions use a nonionic surfactant as the primary surfactant, the compositions have lower irritation potential as compared to traditional anionic-rich cleaning compositions.

Moreover and quite unexpectedly, these compositions are stable even with high concentrations of cationic silicones and/or cationic silanes or silane oligomers. These compositions thus afford increased delivery of cationic conditioning agents in comparison to traditional anionic-based cleaning compositions. When used as shampoos, these compositions deliver conditioner to the hair in a manner in which the conditioner clings to and stays on the hair even after repeated washings. This is believed to be due to the higher quantity of nonionic surfactant in the composition which allows for better compatibility with the above cationic agent(s) and improves overall stability in contrast to classical shampoos. This is true even with charged cationic silicones (e.g., aminodimethicone) or cationic silanes (e.g. aminopropyltriethoxysilane). These classes of charged conditioning agents have typically not been incorporated in traditional shampoo compositions at high concentrations due in part to the strong charge attraction and high degree of complexing between cationic agents and anionic cleaning surfactants which can lead to formation of insoluble salts resulting in unstable compositions. Thus, the low degree of complexing in the current compositions allows for the incorporation of these cationic agents in the present shampoo compositions even though these cationic agents are not typically used in traditional shampoo compositions. Moreover and unexpectedly, the compositions of the invention remain stable even at elevated (e.g. 45° C.) or reduced temperatures (e.g. 4° C.). It also allows for greater deposition of the cationic silicones and/or cationic silanes or silane oligomers onto anionicly charged hair fibers.

All percentages and ratios are calculated by weight unless otherwise indicated. All percentages are calculated based on the total composition unless otherwise indicated.

As used herein, all ranges provided are meant to include every specific range within, and combination of sub ranges between, the given ranges. Thus, a range from 1 to 5, includes 1, 2, 3, 4, and 5 as well as 1-4, 2-4, 1-3, etc.

DEFINITIONS

"About" as used herein means within 10% of the indicated number (e.g. "about 10%" means 9%-11% and "about 2%" means 1.8%-2.2%).

"At least one" as used herein means one or more and thus includes individual components as well as mixtures/combinations.

"Cationic silane oligomer" or "silane oligomer." Silanes, such as alkoxysilanes, may be hydrolyzed in aqueous medium. As used herein, "cationic silane oligomer" or "silane oligomer" means the oligomers that are formed when a cationic silane is hydrolyzed in aqueous medium. This reaction is a hydrolysis and condensation reaction as described in Brochier Salon et al: Kinetics of hydrolysis and self condensation reactions of silanes by NMR spectroscopy. Colloids and Surfaces A: Physicochem. Eng. Aspects 312 (2008) 83-91. Hence, when referring to the final inventive compositions applicants contemplate the presence of the silane and/or its oligomers.

"Clear" as used herein means that the composition is visually clear (a person is able to see through the composition with their naked eyes). It also means that the composition does not exhibit phase separation. The clarity of a formulation can be measured by the transmittance percentage of light with a wavelength of 700 nm by UV-Visible spectrophotometry. "Clear" samples allow for about 60% or higher, more preferably about 70% or higher, even more preferably about 80% or higher, of the light to pass through the formula.

"Comprising" as used herein is used in the inclusive sense of "having" or "including" and not in the exclusive sense of "consisting only of."

"Conditioning" as used herein means imparting to hair at least one property chosen from compatibility, manageability, moisture-retentivity, luster, shine, and softness. The state of conditioning is evaluated by measuring, and comparing the ease of combing of the treated hair in contrast with the untreated hair.

"Good foam" means that the foam produced is in high quantity and is stable and creamy over the period of use.

"HLB" as used herein means the hydrophilic-lipophilic balance of a molecule. It is the ratio between the hydrophilic part and lipophilic part of a molecule. This term is well known to those skilled in the art. See, e.g., "The HLB System: A Time-saving Guide to Emulsifier Selection" (Pub: ICI Americas Inc., 1984) and US2006/0217283 at [0053], both of which, to the extent required, are herein incorporated by reference.

"Keratinous substrates", as used herein, include but are not limited to, skin, hair, lips, eyelashes and nails. A Preferred keratinous substrate is hair.

In an embodiment, the invention relates to an aqueous cleansing composition comprising:
(a) from about 6% to about 20% of at least one nonionic surfactant;
(b) from about 3% to about 10% of at least one amphoteric surfactant;
(c) from about 2% to about 8% of at least one anionic surfactant; and
(d) from about 0.01% to about 5% of at least one cationic silicone, cationic silane, cationic silane oligomer, or a mixture thereof;
wherein the amount of nonionic surfactant (a) present in the final composition is greater than the amount of the amphoteric surfactant (b); and wherein the ratio of nonionic surfactant (a) to anionic surfactant (c) is at least about 1.9:1, by weight, based on the weight percent of each surfactant in the final composition.

Nonionic Surfactants (Component (a))

Non-ionic surfactants, while they are known for good cleaning properties, are not preferred in commercial shampoos in part as they are typically too harsh and drying on keratinous substrates (e.g. hair). However, the ratio of this surfactant to and its association with the amphoteric surfactant of the invention enables the use of non-ionic surfactants in the current cleansing formulation and still yield a conditioning effect.

The at least one nonionic surfactant useful in the cosmetic compositions disclosed herein is selected from: alkyl polyglucosides; ethylene glycol, propylene glycol, glycerol, polyglyceryl esters and their ethoxylated derivatives (herein jointly referred to as "glycol esters"); amine oxides; and mixtures the foregoing.

Alkyl polyglucosides useful in the compositions of the invention include those having the following formula (XX):

$$R^1-O-(R^2O)n-Z(x) \hspace{2cm} (XX)$$

wherein
$R^1$ is an alkyl group having 8-18 carbon atoms;
$R^2$ is an ethylene or propylene group;
Z is a saccharide group with 5 to 6 carbon atoms;
n is an integer from 0 to 10; and
x is an integer from 1 to 5.

Such alkyl poly glucosides useful in the compositions of the invention include lauryl glucoside, octyl glucoside, decyl glucoside, coco glucoside, sucrose laurate, caprylyl/capryl glucoside, sodium lauryl glucose carboxylate, and mixtures thereof. Typically, the at least one alkyl polyglucoside compound is selected from the group consisting of lauryl glucoside, decyl glucoside, coco glucoside, and mixtures thereof, and more typically lauryl glucoside.

Non-limiting examples of glycol esters useful in the compositions of the invention include those described in M. R. Porter et al., Handbook of Surfactants, Ch. 7, §7.12, pp. 231-235 (2$^{nd}$ Ed. 1994), which is herein incorporated by reference. Preferred glycol esters have HLB values between about 9 and about 18. Particular glycol esters useful in the compositions of the invention include PEG-8 glyceryl laurate, polysorbate-40, polyglyceryl-5 laurate, and mixtures thereof. Amine oxides useful in the compositions of the invention include those having the formulas (XXIA) and (XXIB)

R—N(CH3)₂-O     (XXIA), and

R—CO—NH(CH₂)ₙ—N(CH3)₂-O     (XXIB)

wherein
R is an alkyl group having 8-18 carbon atoms; and
n is an integer from 1 to 3
A non-limiting example of a particular amine oxide is lauramine oxide.

In the present compositions, the at least one nonionic surfactant is used in an amount of from about 6% to about 20%, typically from about 7% to about 10%, and more typically about 7.15%, including all ranges and sub ranges therebetween, by weight based on the total weight of the composition as a whole.

Amphoteric Surfactant (Component (b))

The at least one amphoteric surfactant useful in the cosmetic compositions disclosed herein is chosen from betaines, sultaines, amphoacetates, amphoprionates, and mixtures thereof. More typically, betaines and amphoprionates are used, and most typically betaines. Betaines which can be used in the current compositions include those having the formulas (XXIIA-D) below:

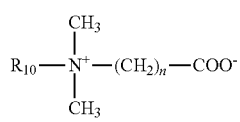

(XXII A-B)

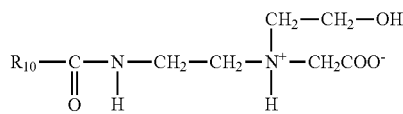

(XXII C)

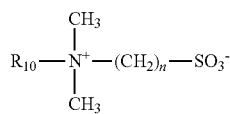

(XXII D)

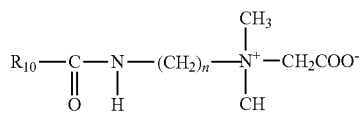

Wherein
$R^{10}$ is an alkyl group having 8-18 carbon atoms; and
n is an integer from 1 to 3.

Particularly useful betaines include, for example, coco betaine, cocoamidopropyl betaine, lauryl betaine, laurylhydroxy sulfobetaine, lauryldimethyl betaine, cocoamidopropyl hydroxysultaine, behenyl betaine, capryl/capramidopropyl betaine, lauryl hydroxysultaine, stearyl betaine, and mixtures thereof. Typically, the at least one betaine compound is selected from the group consisting of coco betaine, cocoamidopropyl betaine, behenyl betaine, capryl/capramidopropyl betaine, lauryl betaine, and mixtures thereof, and more typically cocoamidopropyl betaine.

Hydroxyl sultaines useful in the compositions of the invention include the following

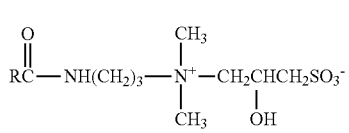

(XXIII)

wherein
R is an alkyl group having 8-18 carbon atoms. Useful alkylamphoacetates include those having the formula (XXIV)

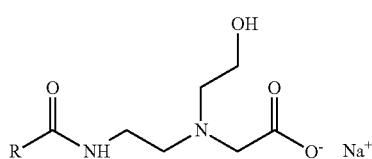

(XXIV)

Wherein
R is an alkyl group having 8-18 carbon atoms. Useful alkyl amphodiacetates include those having the formula (XXV)

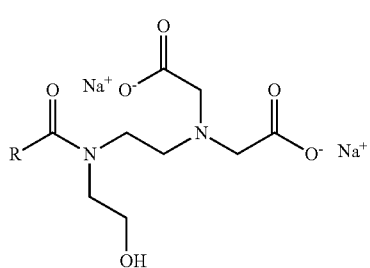

(XXV)

wherein
R is an alkyl group having 8-18 carbon atoms.

In the present compositions, the at least one amphoteric surfactant is used in an amount of from about 3% to about 10% by weight, typically from about 4% to about 8% by weight, and more typically about 5.7% by weight, including all ranges and sub ranges therebetween, based on the total weight of the composition as a whole.

Anionic Surfactant (Component (c))

The at least one anionic surfactant used in the cosmetic compositions disclosed herein can be, for example, chosen from salts, for example, alkali metal salts such as sodium salts, ammonium salts, amine salts, amino alcohol salts and alkaline-earth metal salts, for example magnesium salts, of the following types of compounds: alkyl sulfates, alkyl ether sulfates, acyl isethionates, acyl glycinates, acyl taurates, acyl amino acids, acyl sarcosinates, sulfosuccinates, sulfonates, the alkyl and acyl groups of all these compounds comprising from 6 to 24 carbon atoms (saturated or unsaturated, linear or branched).

Particular sulfate salts useful in the invention include those having the formulas (XXVI A and B)

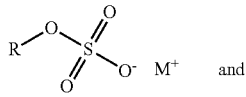 (XXVI A)

and

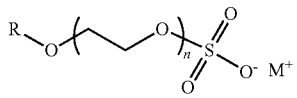 (XXVIB)

wherein
R is alkyl chain having 6 to 24 carbon atoms;
M is an alkali-metal salt as described above; and
n is an integer from 0 to 3.

Non-limiting examples of acyl amino acids, taurates, isethionate, sulfosuccinates and sulfonates useful in the compositions of the invention include those having the following formulas:

Acyl Amino Acids:

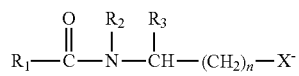 (XXVII)

Taurates:

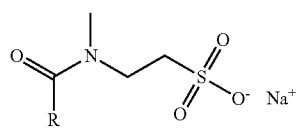 (XXVIII)

Isethionate:

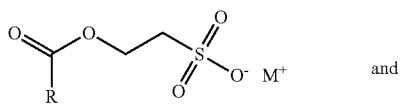 (XXIX A)

and

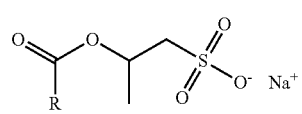 (XXIX B)

Sulfosuccinates:

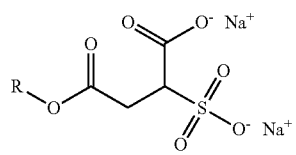 (XXX)

Sulfonates:

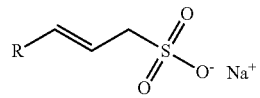 (XXXI)

wherein in the above formulas R, $R^1$, $R^2$ and $R^3$ are each independently selected from H or alkyl chain that has 1-24 carbon atoms, said chain being saturated or unsaturated, linear or branched, and X is COO— or $SO_3$—.

Non-limiting examples of alkyl ether sulfates that can be used in the current compositions include lauryl sulfate, laureth sulfate, and salts and mixtures of these. More particularly, the lauryl sulfate is sodium lauryl sulfate and the laureth sulfate is sodium laureth sulfate.

Non-limiting examples of isethionates that can be used in the current compositions include sodium cocoyl isethionate, sodium lauroyl methyl isethionate, and mixtures thereof.

Non-limiting examples of isethionates that can be used in the current compositions include sodium cocoyl isethionate, sodium lauroyl methyl isethionate, and mixtures thereof.

A non-limiting example of a taurate that can be used in the current compositions is sodium methyl cocoyl taurate.

Acyl amino acids that can be used in the current compositions include amino acid surfactants based on glycine, sarcosine, threonine, glutamine, glutamic acid or alanine. The most common salt ions attached to the at least one acyl amino acid are sodium or potassium. The salt ion attached to the acyl amino acid can also be an organic salt, such as triethanolamine (TEA), or a metal salt. Examples of acyl amino acid compounds include, but are not limited to, sodium cocoyl glycinate, potassium cocoyl glycinate, sodium lauryl sarcosinate, sodium cocoyl alaninate, and salts thereof, and mixtures thereof. Typically, the at least one acyl amino acid is selected from the group consisting of sodium cocoyl glycinate, potassium cocoyl glycinate, and mixtures thereof, and in particular sodium cocoyl glycinate.

A non-limiting example of a sulfosuccinate that can be used in the current compositions is disodium laurel sulfosuccinate.

A non-limiting example of a sulfonate that can be used in the current compositions is sodium C14-16 olefin sulfonate.

The at least one anionic surfactant is present in a total amount ranging from about 2% to about 8% by weight, typically from about 2.5% to about 5%, more typically 3% by weight, including all ranges and sub ranges therebetween, based on the total weight of the composition as a whole.

Cationic Silicones and Cationic Silanes (Component (d))

In this application, cationic silicones and cationic silanes are also jointly referred to as "conditioning agents" or "cationic conditioning agents."

Non-limiting examples of cationic silicones that can be used in the current compositions include amino silicones of varying molecular weights.

Amino Silicones

The term "amino silicone" means any polyaminosiloxane, i.e. any polysiloxane comprising at least one primary, secondary or tertiary amine function or a quaternary ammonium group. Preferably, the amino silicone(s) used in the cosmetic composition according to the present invention are selected from (A)-(D) as described below.

Amino silicones are described, for example, in US2011/0155163 and US2011/155164, both of which are herein incorporated by reference.

(A) Compounds Corresponding to Formula (II)

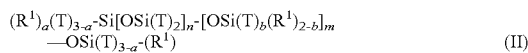

in which:

T is a hydrogen atom or a phenyl, hydroxyl (—OH) or $C_1$-$C_8$ alkyl radical, and preferably methyl, or a $C_1$-$C_8$ alkoxy, preferably methoxy, a denotes the number 0 or an integer from 1 to 3, and preferably 0, b denotes 0 or 1, and in particular 1, m and n are numbers such that the sum (n+m) can range especially from 1 to 2000 and in particular from 50 to 150, it being possible for n to denote a number from 0 to 1999 and in particular from 49 to 149, and for m to denote a number from 1 to 2000 and in particular from 1 to 10;

$R^1$ is a monovalent radical of formula —$C_qH_{2q}$L in which q is a number from 2 to 8 and L is an optionally quaternized amino group selected from the following groups:

—N($R^2$)—$CH_2$—$CH_2$—N($R^2$)$_2$;
—N($R^2$)$_2$; —N$^+$($R^2$)$_3$Q$^-$;
—N$^+$($R^2$)(H)$_2$Q$^-$;
—N$^+$($R^2$)$_2$HQ$^-$;
—N($R^2$)—$CH_2$—$CH_2$—N$^+$($R^2$)(H)$_2$Q$^-$, in which $R^2$ denotes a hydrogen atom, a phenyl, a benzyl or a saturated monovalent hydrocarbon-based radical, for example a $C_1$-$C_{20}$ alkyl radical, and Q$^-$ represents a halide ion, for instance fluoride, chloride, bromide or iodide.

In particular, the amino silicones corresponding to the definition of formula (II) are selected from the compounds corresponding to formula (III) below:

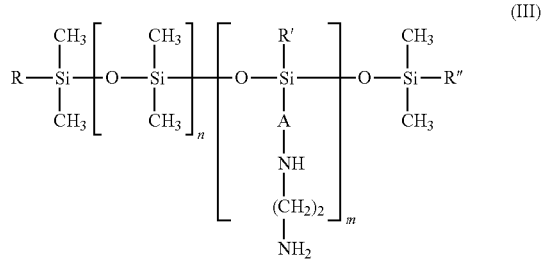

in which R, R' and R", which may be identical or different, denote a $C_1$-$C_4$ alkyl radical, preferably $CH_3$; a $C_1$-$C_4$ alkoxy radical, preferably methoxy; or OH; A represents a linear or branched, $C_3$-$C_8$ and preferably $C_3$-$C_6$ alkylene radical; m and n are integers dependent on the molecular weight and whose sum is between 1 and 2000.

According to a first possibility, R, R', R", which may be identical or different, represent a $C_1$-$C_4$ alkyl or hydroxyl radical, A represents a $C_3$ alkylene radical and m and n are such that the weight-average molecular weight of the compound is between 5000 and 500 000 approximately. Compounds of this type are referred to in the CTFA dictionary as "aminodimethicones".

According to a second possibility, R, R' and R", which may be identical or different, represent a $C_1$-$C_4$ alkoxy or hydroxyl radical, at least one of the radicals R or R" is an alkoxy radical and A represents a $C_3$ alkylene radical. The hydroxy/alkoxy molar ratio is preferably between 0.2/1 and 0.4/1 and advantageously equal to 0.3/1. Moreover, m and n are such that the weight-average molecular weight of the compound is between 2000 and $10^6$. More particularly, n is between 0 and 999 and m is between 1 and 1000, the sum of n and m being between 1 and 1000.

In this category of compounds, mention may be made, inter alia, of the product BELSIL® ADM 652 sold by Wacker.

According to a third possibility, R and R", which are different, represent a $C_1$-$C_4$ alkoxy or hydroxyl radical, at least one of the radicals R or R" is an alkoxy radical, R' represents a methyl radical and A represents a $C_3$ alkylene radical. The hydroxy/alkoxy molar ratio is preferably between 1/0.8 and 1/1.1 and advantageously equal to 1/0.95. Moreover, m and n are such that the weight-average molecular weight of the compound is between 2000 and 200 000. More particularly, n is between 0 and 999 and m is between 1 and 1000, the sum of n and m being between 1 and 1000.

More particularly, mention may be made of the product FLUID WR® 1300 sold by Wacker.

According to a fourth possibility, R and R" represent a hydroxyl radical, R' represents a methyl radical and A is a $C_4$-$C_8$ and preferably $C_4$ alkylene radical. Moreover, m and n are such that the weight-average molecular weight of the compound is between 2000 and $10^6$. More particularly, n is between 0 and 1999 and m is between 1 and 2000, the sum of n and m being between 1 and 2000.

A product of this type is especially sold under the name DC 28299 by Dow Corning.

The molecular weight of these silicones is determined by gel permeation chromatography (ambient temperature, polystyrene standard; µ styragem columns; eluent THF; flow rate 1 mm/m; 200 µl of a solution containing 0.5% by weight of silicone in THF are injected, and detection is performed using a refractometer and a UV meter).

A particular product of formula (I) is the polymer known in the CTFA dictionary (7th edition, 1997) as "trimethylsilylamodimethicone", corresponding to formula (IV)

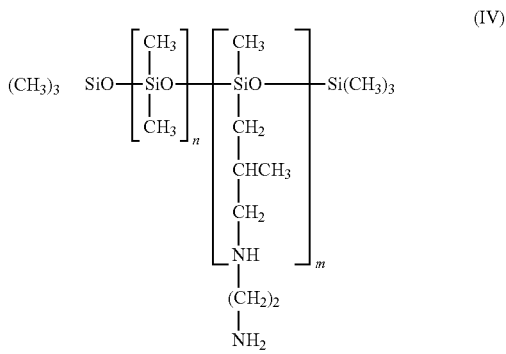

in which n and m have the meanings given above in accordance with formula (II) or (III) above.

Such compounds are described, for example, in EP 0 095 238, which is herein incorporated by reference. A compound of formula (IV) is sold, for example, under the name Q2-8220 by the company OSI.

(B) the Second Type of Amino Silicone Compounds Correspond to Formula (V)

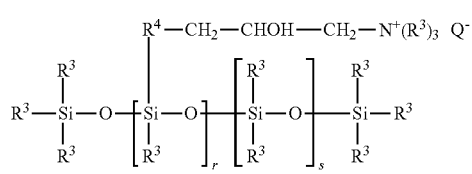

in which:

$R^3$ represents a $C_1$-$C_{18}$ monovalent hydrocarbon-based radical, and in particular a $C_1$-$C_{18}$ alkyl or $C_2$-$C_{18}$ alkenyl radical, for example methyl;

$R^4$ represents a divalent hydrocarbon-based radical, especially a $C_1$-$C_{18}$ alkylene radical or a divalent $C_1$-$C_{18}$, and for example $C_1$-$C_8$, alkylenoxy radical;

$Q^-$ is a halide ion, in particular chloride;

r represents a mean statistical value from 2 to 20 and in particular from 2 to 8;

s represents a mean statistical value from 20 to 200 and in particular from 20 to 50.

Such compounds are described more particularly in U.S. Pat. No. 4,185,087, which is herein incorporated by reference.

A compound falling within this class is the product sold by the company Union Carbide under the name Ucar Silicone ALE 56.

(C) Quaternary Ammonium Silicones of Formula (VI) are Another Type of Silicone Useful in the Invention:

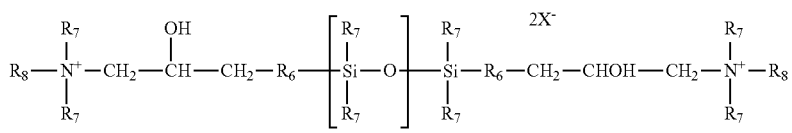 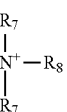

in which:

$R_7$, which may be identical or different, represent a monovalent hydrocarbon-based radical containing from 1 to 18 carbon atoms, and in particular a $C_1$-$C_1$ alkyl radical, a $C_2$-$C_{18}$ alkenyl radical or a ring comprising 5 or 6 carbon atoms, for example methyl;

$R_6$ represents a divalent hydrocarbon-based radical, especially a $C_1$-$C_{18}$ alkylene radical or a divalent $C_1$-$C_{18}$, and for example $C_1$-$C_8$, alkylenoxy radical linked to the Si via an SiC bond;

$R_8$, which may be identical or different, represent a hydrogen atom, a monovalent hydrocarbon-based radical containing from 1 to 18 carbon atoms, and in particular a $C_1$-$C_{18}$ alkyl radical, a $C_2$-$C_{18}$ alkenyl radical or a radical —$R_6$—NH-CO$R_7$;

$X^-$ is an anion such as a halide ion, especially chloride, or an organic acid salt (acetate, etc.); and r represents a mean statistical value from 2 to 200 and in particular from 5 to 100.

These silicones are described, for example, in patent application EP-A 0 530 974, which is herein incorporated by reference.

An example of the compound of formula (VI) is the product referenced in the CTFA dictionary (1997 edition) as Quaternium 80. Such a product is marketed by the company Evonik Goldschmidt under the names ABIL QUAT 3272 or 3474.

(D) Formula (VII) Below Provides Another Example of Amino Silicones Useful in the Invention:

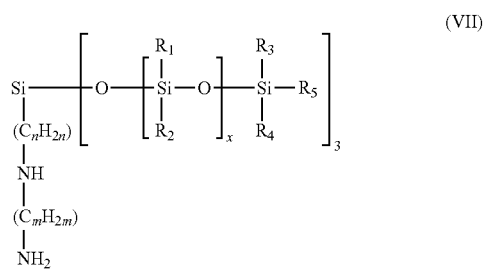

in which:

$R_1$, $R_2$, $R_3$ and $R_4$, which may be identical or different, denote a $C_1$-$C_4$ alkyl radical or a phenyl group, $R_5$ denotes a $C_1$-$C_4$ alkyl radical or a hydroxyl group, n is an integer ranging from 1 to 5, m is an integer ranging from 1 to 5, and in which x is selected such that the amine number is between 0.01 and 1 meq/g.

Amino silicone(s) that are particularly useful in the invention include polysiloxanes containing amine groups, such as the compounds of formula (III) or of formula (IV), and even more particularly the silicones containing quaternary ammonium groups of formula (VI).

Non-limiting examples of particularly useful silicones include aminodimethicones, such as the products available from the company Wacker under the name FLUID® (for example FLUID® WR 1300) and BELSIL® (for example BELSIL® ADM LOG1) and a product available from Momentive Performance Material under the name SILSOFT®. Also useful is trimethylsilylamodimethicone (such as Q@-8220 available from OSI).

Silane Compounds

Exemplary silanes that may be used according to various embodiments of the disclosure include, but are not limited to, organosilanes and derivatives thereof, such as alkylsilanes, allylsilanes, and alkoxysilanes.

In various exemplary embodiments, the at least one silane compound may be chosen from alkoxysilanes comprising at least one solubilizing functional group, such as for example, methoxysilanes, triethoxysilanes, aminopropyltriethoxysilane, methyltriethoxysilane, and derivatives thereof and mixtures thereof.

As used herein, the term "at least one solubilizing functional group" means any functional chemical group facilitating the bringing into solution of the alkoxysilane in the solvent or in a combination of solvents of the composition, for example, in solvents chosen from water, water-alcoholic mixtures, organic solvents, polar solvents and non-polar solvents.

Suitable solubilizing functional groups include, but are not limited to, primary, secondary, and tertiary amine, aromatic amine, alcohol, carboxylic acid, sulfonic acid, anhydride, carbamate, urea, guanidine, aldehyde, ester, amide, epoxy, pyrrole, dihydroimidazole, gluconamide, pyridyle, and polyether groups.

In an embodiment the at least one alkoxysilane comprising at least one solubilizing functional group may comprise two or three alkoxy functions. In another embodiment, the alkoxy functional groups are chosen from methoxy and ethoxy functional groups.

According to a further embodiment, the at least one alkoxysilane comprising at least one solubilizing functional group present in the composition of the present disclosure is chosen from compounds of formula (VIII):

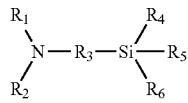

wherein,
$R_4$ is chosen from halogen atoms, OR' groups, and $R_{11}$ groups;
$R_5$ is chosen from halogen atoms, OR" groups, and $R_{12}$ groups;
$R_6$ is chosen from halogen atoms, OR'" groups, and $R_{13}$ groups;
$R_1$, $R_2$, $R_3$, R', R", R'", $R_{11}$, $R_{12}$, and $R_{13}$, which may be identical or different, are chosen from linear and branched, saturated and unsaturated hydrocarbon groups, optionally bearing at least one additional chemical group, wherein $R_1$, $R_2$, R', R", and R'" may also be chosen from hydrogen;
provided that at least two groups $R_4$, $R_5$, and $R_6$ are different from $R_{11}$, $R_{12}$, and $R_{13}$, and at least two groups R', R", and R'" are not hydrogen.

The at least one alkoxysilane comprising at least one solubilizing functional group may also be chosen from compounds of formula (IX):

wherein,
$R_9$ is chosen from halogen atoms and $OR'_9$ groups;
$R_{10}$ is chosen from halogen atoms and $OR'_{10}$ groups;
$R'_9$ and $R'_{10}$, which may be identical or different, are chosen from hydrogen, and linear and branched, saturated and unsaturated $C_1$-$C_{14}$ hydrocarbon groups;
$R_7$ is a non hydrolyzable functional group providing a cosmetic effect; and
$R_8$ is a non hydrolyzable functional group bearing at least one function chosen from amines, carboxylic acids and salts thereof, sulfonic acids and salts thereof, polyols such as glycol, polyethers such as polyalkylene ether, and phosphoric acids and salts thereof; and
provided that at least one of $R_9$ and $R_{10}$ is not a halogen;

As used herein, the term "functional group providing a cosmetic effect" means a group derived from an entity chosen from reducing agents, oxidizing agents, coloring agents, polymers, surfactants, antibacterial agents, and UV absorbing filters.

According to a third embodiment, the at least one alkoxysilane comprising at least one solubilizing functional group may be chosen from compounds of formula (X):

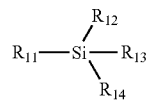

wherein,
$R_{12}$ is chosen from halogen atoms, $OR'_{12}$ groups, and $R_o$ groups;
$R_{13}$ is chosen from halogen atoms, $OR'_{13}$ groups, and $R'_o$ groups;
$R_{14}$ is chosen from halogen atoms, $OR'_{14}$ groups, and $R''_o$ groups;
$R_{11}$ is chosen from groups bearing at least one function chosen from carboxylic acids and salts thereof, sulfonic acids and salts thereof, and polyalkylethers;
Ro, R'o, R"o, $R'_{12}$, $R'_{13}$, and $R'_{14}$, which may be identical or different, are chosen from linear and branched, saturated and unsaturated, $C_1$-$C_{14}$ hydrocarbon groups optionally bearing at least one additional chemical functional group chosen from carboxylic acids and salts thereof, sulfonic acids and salts thereof, and polyalkylether functions, and wherein $R'_{12}$, $R'_{13}$, and $R_{14}$ may also be chosen from hydrogen;
provided that at least two groups from $R_{12}$, $R_{13}$ and $R_{14}$ are different from $R_o$, $R'_o$, and $R''_o$ groups; and
provided further that at least two of the groups $R'_{12}$, $R'_{13}$, and $R'_{14}$ are not hydrogen.

According to another embodiment, the at least one alkoxysilane comprising at least one solubilizing functional group may be chosen from compounds of formula (XI):

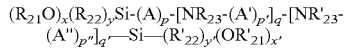

wherein,
$R_{21}$, $R_{22}$, $R'_{21}$, and $R'_{22}$, which may be identical or different, are chosen from linear and branched, saturated and unsaturated hydrocarbon chains, optionally comprising at least one heteroatom, optionally interrupted by or substituted with at least one group chosen from ether, ester, amine, amide, carboxyl, hydroxyl, and carbonyl groups;
x is an integer ranging from 1 to 3;
y is 3-x;
x' is an integer ranging from 1 to 3;
y' is 3-x',
p, p', p", q, and q' can each be 0 or 1, wherein at least one of q or q' is not equal to zero;
A, A', and A", which may be identical or different, are chosen from linear and branched $C_1$-$C_{20}$ alkylene divalent radicals; and
$R_{23}$ and $R'_{23}$, which may be identical or different, are chosen from hydrogen and linear and branched, saturated and unsaturated hydrocarbon chains, optionally comprising at least one heteroatom, optionally interrupted by or substituted with at least one entity chosen from ether, $C_1$-$C_{20}$ alcohol ester, amine, carboxyl, alkoxysilane, $C_6$-$C_{30}$ aryl, hydroxyl, and carbonyl groups, and aromatic, heterocyclic, and non-heterocyclic rings, optionally substituted with at least one group chosen from $C_3$-$C_{20}$ alcohol ester, amine, amide, carboxyl, alkoxysilane, hydroxyl, carbonyl, and acyl groups.

The at least one alkoxysilane comprising at least one solubilizing functional group may also be chosen from compounds of formula (XII):

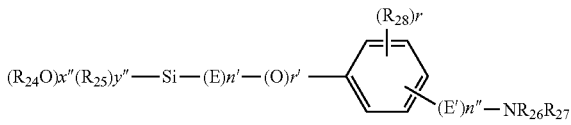

wherein,
- $R_{24}$ and $R_{25}$, which may be identical or different, are chosen from linear and branched, saturated and unsaturated hydrocarbon chains, optionally comprising at least one heteroatom, optionally interrupted by or substituted with at least one group chosen from ether, ester, amine, amide, carboxyl, hydroxyl, and carbonyl groups;
- x" is 2 or 3;
- y" is 3-x";
- n' is 0 or 1;
- n" is 0 or 1;
- E and E', which may be identical or different, are chosen from linear and branched $C_1$-$C_{20}$ alkylene divalent radicals;
- $R_{26}$ and $R_{27}$, which may be identical or different, are chosen from hydrogen and linear and branched, saturated and unsaturated hydrocarbon chains, optionally comprising at least one heteroatom, optionally interrupted by or substituted with at least one entity chosen from ether, $C_1$-$C_2$, alcohol ester, amine, carboxyl, alkoxysilane, $C_6$-$C_{30}$ aryl, hydroxyl, and carbonyl groups, and aromatic, heterocyclic, and non-heterocyclic rings, optionally substituted with at least one group chosen from $C_1$-$C_{20}$ alcohol ester, amine, amide, carboxyl, alkoxysilane, hydroxyl, carbonyl, and acyl groups;
- r is an integer ranging from 0 to 4;
- r'=0 or 1; and
- $R_{28}$ is chosen from hydrogen and linear and branched, saturated and unsaturated hydrocarbon chains, comprising, optionally at least one heteroatom, optionally interrupted by or substituted with at least one entity chosen from ether, alkyl alcohol ester, amine, carboxyl, alkoxysilane, alkyl aryl, hydroxyl, and carbonyl groups, and aromatic, heterocyclic, and non-heterocyclic rings.

According to a further exemplary embodiment, the at least one alkoxysilane comprising at least one solubilizing functional group may be chosen from compounds of formula (XIII):

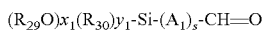

wherein,
- $R_{29}$ and $R_{30}$, independently, are chosen from linear and branched, saturated and unsaturated hydrocarbon chains, optionally comprising at least one heteroatom, optionally interrupted by or substituted with at least one group chosen from ether, ester, amine, amide, carboxyl, hydroxyl, and carbonyl groups;
- $x_1$ is 2 or 3;
- $y_1$ is 3-$x_1$;
- $A_1$ is chosen from linear and branched $C_1$-$C_{20}$ alkylene divalent radicals, optionally interrupted by or substituted with at least one group chosen from $C_1$-$C_{30}$ alcohol ester, amine, carboxyl, alkoxysilane, $C_6$-$C_{30}$ aryl, hydroxyl, and carbonyl groups; and
- s is 0 or 1.

In a further exemplary embodiment, the at least one alkoxysilane comprising at least one solubilizing functional group is chosen from compounds of formula (XIV):

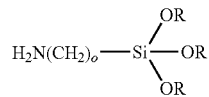

wherein the R radicals, which may be identical or different, are chosen from $C_1$-$C_6$ alkyl radicals and n is an integer ranging from 1 to 6, for example, from 2 to 4.

The alkoxysilanes useful in the present disclosure can be chosen from alkoxysilanes comprising a silicon atom in a formula $R_{(4-n)}SiX_n$, wherein X is a hydrolysable group such as methoxy, ethoxy or 2-methoxyethoxy, R is a monovalent organic radical which contains 1 to 12 carbon atoms and may contain groups such as mercapto, epoxy, acrylyl, methacrylyl, amino or urea, and n is an integer from 1 to 4, and according to at least one embodiment is 3. Exemplary alkoxysilanes include, but are not limited to, 3-mercaptopropyltriethoxysilane and aminoalkyltrialkoxysilanes such as 3-aminopropyltriethoxysilane, as described in French Patent Application No. FR2789896, incorporated by reference herein.

Other useful alkoxysilanes are cited, for example, in EP1216022, incorporated by reference herein, which describes alkoxysilanes comprising at least one hydrocarbon chain containing a non-basic solubilizing chemical function. In this respect, non-limiting mention may be made of the HCl-neutralized sodium N-[(3-trimethoxysilyl)propyl]ethylenediaminetriacetate supplied by GELEST.

In an embodiment, the alkoxysilanes may comprise at least one hydrocarbon chain containing fluorine atoms. Possible examples include but are not limited to the 3,3,3-trifluoropropyltriethoxysilane or tridecafluorooctyltriethoxysilane compounds described in EP1510197, incorporated by reference herein.

In another embodiment, the useful alkoxysilanes may be alkoxysilanes that carry a group having a cosmetic functional group. Such cosmetic functional group can be an aromatic nitro dye or anthraquinone, napthoquinone, benzoquinone, azo, xanthene, triarylmethane, azine, indoaniline, indophenolic or indoamine dye.

Another cosmetic functional group is a group having a reductive effect, such as thiol groups, sulphinic acid or sulphinic salt.

It is also contemplated that these alkoxysilanes may carry a solubilizing, non-hydrolysable group such as amino groups, carboxylic acids, sulphonic acids, sulphates, quaternary ammoniums, polyalcohols, polyether and phosphates. One possible example of the foregoing types of alkoxysilanes is aminopropyl-N-(4,2-dinitrophenyl)aminopropyldiethoxysilane. Additional exemplary compounds of this type are described, for example, in EP1216023, which is herein incorporated by reference.

Non-limiting examples of useful alkoxysilanes include 3-mercaptopropyltriethoxysilane and aminoalkyltrialkoxysilanes such as 3-aminopropyltriethoxysilane ("APTES", described in French Patent Application No. FR 2 789 896, incorporated herein by reference), and mixtures thereof.

The at least one cationic silicone and/or silane and/or silane oligomer(s) is present in the compositions of the invention in an amount of from about 0.01% to about 5% by weight, typically from about 0.1% to about 3% by weight, and more typically from about 0.25% to about 2%, by weight, including all ranges and sub ranges therebetween, the weight being calculated based on the total weight of the composition as a whole. In a particular embodiment, the amount of cationic conditioning polymer is present at about 1% by weight.

Additives

The composition of the present disclosure may additionally include any other adjuvant or additive that is usually used in the field of self-cleaning products, in particular shampoos. A person skilled in the art would know which adjuvants and/or additives to select to achieve the desired results (e.g. preservatives) without adversely affecting the properties of claimed emulsions. For example, such additives include pH adjusting agents, preserving agents, sequestrants and chelators, consistency regulators (e.g. isopropyl alcohol), thickeners, pH-regulators, antioxidants, fragrances, dyestuffs such as soluble dyes and pigments, optical brighteners, electrolytes and stabilizers (e.g. sodium chloride, glycerin), plant extracts, proteins, amino acids, vitamins, glycols, emollients, derivatives of the foregoing, and mixtures thereof. Such additives are described, for example in US2012/0308492 at [0079]-[0080] and US2006/0217283 at [0084]-[0087], herein incorporated by reference. These additives may be hydrophobic or hydrophilic.

Non-limiting examples of pH adjusting agents includes potassium acetate, potassium hydroxide, sodium carbonate, sodium hydroxide, phosphoric acid, succinic acid, sodium citrate, citric acid, boric acid, lactic acid, sodium hydrogen carbonate, ethanol amines, and mixtures thereof. In a particular embodiment, the pH adjusting agent is selected from potassium hydroxide, sodium hydroxide, ethanol amines, and mixtures thereof. In a particular embodiment, the pH adjusting agent is selected from sodium hydroxide, potassium hydroxide and ethanol amines, and mixtures thereof.

Non-limiting examples of useful preservatives include ethanol, polyvinyl alcohol, phenoxyethanol, benzyl alcohol, salicylic acid, sodium benzoate, benzoic acid, caprylyl glycol, methyl paraben, propyl paraben, ethylhexylglycerin, 1,3-propanediol, cholorphensin, methylchloroisothiazolinone, methylisothiazolinone, benzalkonium chloride, polyaminopropyl biguanide, and mixtures thereof. In a particular embodiment, the pH adjusting agent is selected from cholorphensin, methylchloroisothiazolinone, methylisothiazolinone, benzalkonium chloride, polyaminopropyl biguanide, and mixtures thereof.

Chelating agents and antioxidants are ingredients which assist in preventing or retarding spoilage. Examples of antioxidants suitable for use in the present composition are potassium sulfite, sodium bisulfite, sodium erythrobate, sodium metabisulfite, sodium sulfite, propyl gallate, cysteine hydrochloride, butylated hydroxytoluene, butylated hydroxyanisole, and mixtures thereof. Suitable chelators include salts of ethylenediaminetetraacetic acid ("EDTA"), tetrasodium EDTA, butylated hydroxytoluene ("BHT"), and mixtures thereof.

The cleansing compositions of the present invention have a pH of from about 5 to about 9, more typically between about 6 and about 8. Additionally, the cleansing compositions are preferably clear.

The present cleansing composition has a viscosity of about 2500 cPs to about 30000 cPs, typically from about 3000 cPs to about 20,000 cPs, and more particularly from about 3000 cPs to about 6000 cPs, more likely from about 4000 cPs to about 6000 cPs, including all ranges and sub ranges therebetween, measured using Brookfield viscometer as discussed below in the examples.

In an embodiment, the present invention relates to an aqueous cleaning and conditioning composition comprising:

(a) from about 6% to about 20% of at least one nonionic surfactant selected from alkyl polyglucosides and glycol esters, and mixtures thereof;
(b) from about 3% to about 10% of at least one amphoteric surfactant selected from betaines, sultaines, amphoacetates, amphoprorionates, and mixtures thereof;
(c) from about 2% to about 8% of at least one anionic surfactant selected from lauryl sulfates, laureth sulfates, isethionates, glutamates, alaninates, glycinates, taurates, acyl amino acids, sarcosinates, sulfosuccinates, sulfonates, alkyl polyglucoside sulfonates and alkyl polyglucoside carboxylates, and mixtures thereof; and
(d) from about 0.01% to about 5% of at least one cationic silicone, cationic silane, cationic silane oligomer formed by the hydrolysis of a cationic silane in water, or a mixture thereof;
wherein the amount of nonionic surfactant (a) present in the final composition is greater than the amount of the amphoteric surfactant (b); and wherein the ratio of nonionic surfactant (a) to anionic surfactant (c) is at least about 1.9:1, by weight, based on the weight percent of each surfactant in the final composition.

In an embodiment, the ratio of the amount of nonionic surfactant (a) present in the final composition to the amount of anionic surfactant (c) is from about 1.9:1 to about 16:1, more typically from about 2:1 to about 10:1, particularly from about 2:1 to about 5:1, and more particularly about 2.4:1, including all ranges and sub ranges therebetween.

In a particular embodiment, the present invention relates to an aqueous cleaning and conditioning composition comprising:

(a) from about 6% to about 20% of at least one nonionic surfactant selected from lauryl glucoside, decyl glucoside, and mixtures thereof;
(b) from about 3% to about 10% of at least one amphoteric surfactant selected from cocoamphopropionate, cocoamidopropyl betaine, and mixtures thereof;
(c) from about 2% to about 8% of at least one anionic surfactant selected from sodium cocoyl taurate, sodium cocoyl glycinate, sodium cocoyl taurate, and sodium laureth sulfate, and mixtures thereof; and
(d) from about 0.01% to about 5% of at least one cationic silicone or cationic silane selected from aminodimethicone and 3-aminopropyltriethoxysilane, including oligomers of 3-aminopropyltriethoxysilane formed when the 3-aminopropyltriethoxysilane is hydrolyzed in water, and mixtures thereof;

wherein the amount of nonionic surfactant (a) present in the final composition is greater than the amount of the amphoteric surfactant (b); and the ratio of nonionic surfactant (a) to anionic surfactant (c) is from about 1.9:1 to about 5:1, based on the weight percent of each surfactant in the final composition.

The present invention is also directed to a process for cleansing and conditioning a keratinous substrate involving contacting the keratinous substrate with the above-disclosed cleansing composition. Preferably the keratinous substrate is hair.

It has also been found that the current formulation also increases/improves the deposition of hydrophobic non-ionic conditioning agents, for example silicones and oils, onto a keratinous substrate. Thus, in another embodiment, the invention is also directed to a method of increasing the deposition of hydrophobic non-ionic conditioning agents onto a keratinous substrate comprising contacting the keratinous substrate with a non-ionic conditioning agent and a composition of the invention.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis unless otherwise specified.

EXAMPLES

Preparation

The compositions of the examples below were prepared by adding the nonionic, amphoteric and anionic surfactants to water and mixing while hearing to 50° C. until the mixture was uniform. To the extent used, fragrances, preservatives and conditioning agent(s) were then added. All of the compositions in the examples 1 and 2 were clear gel-like compositions. Depending on the surfactants used, the compositions were colorless, yellow or brownish. Clarity of the compositions was measured by the transmittance percentage of light with a wavelength of 700 nm by UV-visible spectrophotometry.

TABLE 1

Examples 1-4: Compositions Having Various Surfactan Substitutions

| Ingredient category | INCI Name | Ex 1 | Ex 2 | Ex 3 | Ex 4 |
|---|---|---|---|---|---|
| Water, Preservatives, Dyes, Fragrance | | QS | QS | QS | QS |
| Nonionic surfactant (a) | LAURYL GLUCOSIDE | 7.15 | 7.15 | 7.15 | 7.15 |
| Amphoteric surfactant (b) | COCAMIDOPROPYL BETAINE | 5.7 | 5.7 | 5.7 | 5.7 |
| Anionic Surfactant (c) | SODIUM COCOYL GLYCINATE | 3 | 3 | 3 | 3 |
| Conditioning agent (d) | 3-AMINOPROPYL-TRIETHOXYSILANE | 1 | 2 | 5 | |
| Conditioning agent (d) | AMINODIMETHICONE | | | | 1 |

As is shown in Table 1 above, the compositions of the invention (Examples 1-4 and 4) can accommodate higher amounts (e.g. 1% or higher) of cationic sicones and silanes that are not typically found in currently available commercial shampoo formulations and still remain stable.

Evaluation Protocols

Stability:

The composition of Example 1 was stored at reduced temperatures (4-6° C.), elevated temperatures (37-50° C.) and room temperature for at least 8 weeks. Properties evaluated included visual inspection (phase separation), stability of pH, and stability of acceptable usage viscosity 2000-40,000 cps measured using a Brookfield viscometer. A product was considered stable if it passed all 3 criteria of testing.

The Results for Example 1 are as follows:
Transmittance of light at 700 nm=90%
Initial viscosity: 4200 cps
8 week viscosity: 3910 cps
Appearance: clear and viscous liquid.

Cationic Deposition Study:

Deposition of cationic silicone or silane was studied using an established method in the art referred to as the rubine dye test. The test uses an anionic red dye (red 80) which adsorbs onto the cationic changes left on the hair after rinse. Qualitative or quantitative deposition is determined by the amount of red dye remaining on the hair fibers after rinse.

The protocol for treating and staining the swatches is:

Hair is rinsed under warm water.

Product is applied and lathered for 30 seconds.

Product is rinsed under warm water.

Hair swatches are submerged into dye solution proportional to the weight of the hair swatch and allowed to soak for 30 seconds.

Dye solution is rinsed for 30 second under warm water.

Swatches are allowed to air dry before comparison.

Hair swatches treated with the composition of Example 1, a state of the art shampoo containing the same silane molecule (Example 3), and a control shampoo not containing a cationic silicone or silane were subjected to cationic deposition studies following the above protocol. The increased "redness" of the hair in a swatch demonstrates the increased retention of cationic agent (APTES) on to the hair swatch after rinsing. The results of this test are summarized in Table 2 below.

TABLE 2

Cationic Deposition Comparison

| Product | Description of swatch | Result |
|---|---|---|
| Control cleansing shampoo (no cationic conditioner) | Gray hair was unstained | Negative Result - No color (no cationic deposition) |
| Comparative state of the art shampoo with 0.75% APTES | Gray hair was unstained | Negative Result - No color (no cationic deposition) |
| Example 1 (1% APTES) (1% silane) | Gray hair was stained with pink shade, | Positive Result - pink coloring indicates cationic deposition |

The data in Table 2 demonstrates that the hair swatch treated with the inventive composition of Example 1 shows the highest level of conditioning effect (highest level of cationic conditioning agent deposition) in this comparative test.

Quantification of Silicone Deposition onto Hair Swatches:

Cationic deposition was further quantified by Inductively Coupled Plasma Optical Emission Spectroscopy (ICP-OES). For this experiment, different formulations were examined. The same lot of hair was treated with each formulation for 1, 5 and 10 washings. The silicon uptake concentration detected by the instrument directly correlates to deposition of elemental silicon throughout the hair fiber. APTES was the only molecule containing elemental silicon in all formulations tested. The results of this experiment are provided below in Table 3.

Protocol for Washing the Swatches:

Prior to analytical testing, each of the hair swatches was rinsed with water for 30 seconds to wet the hair. The test formulation was then applied to each respective hair swatch, lathered for 30 seconds and allowed to rest for one minute. The swatches were then rinsed with water for 30 seconds. All samples were initially treated once with clarifying shampoo that does not contain any cationic ingredient prior to silane shampoo treatment.

TABLE 3

| Sample | Amount APTES/ Number of Washes | Silicon Deposition (ppm) |
| --- | --- | --- |
| Clarifying shampoo | Clarifying shampoo | 270 |
| Control | 0% APTES- 1 Wash | 190 |
| Control | 0% APTES- 5 Washings | 162 |
| Control | 0% APTES- 10 Washings | 160 |
| State of the art | 0.75% APTES- 1 Wash | 210 |
| State of the art | 0.75% APTES- 5 Washings | 253 |
| State of the art | 0.75% APTES- 10 Washings | 268 |
| Ex 1 | 1% APTES- 1 Wash | 720 |
| Ex 1 | 1% APTES- 5 Washings | 1571 |
| Ex 1 | 1% APTES- 10 Washings | 2417 |
| Ex 2 | 2% APTES- 1 Wash | 1312 |
| Ex 2 | 2% APTES- 5 Washings | 2587 |
| Ex 2 | 2% APTES- 10 Washings | 3450 |

The data in Table 3 demonstrates an increase in silicon deposition with successive application of APTES-containing compositions according to the invention (Examples 1 and 2) as well as with increased APTES concentration in those compositions.

The data in Table 3 also shows that repeated application of the compositions of the invention (5 and 10 washes) affords increased deposition of silicon-based ingredient(s) onto the hair. This increased deposition of silicon-based ingredient(s) provides progressive conditioning benefits, such as progressive smoothing and strengthening.

What is claimed is:

1. An aqueous cleansing composition comprising:
   (a) from about 6% to about 20% of at least one nonionic surfactant that is an alkyl polyglucoside;
   (b) from about 3% to about 10% of at least one amphoteric surfactant selected from the group consisting of betaines, sultaines, amphoacetates, amphoproprionates, and mixtures thereof;
   (c) from about 2% to about 8% of at least one anionic surfactant; and
   (d) from about 0.01% to about 5% of at least one cationic silane, cationic silane oligomer, or a mixture thereof selected from the group consisting of an alkoxysilane, and oligomer of the alkoxysilane, and mixtures thereof;
   wherein the amount of nonionic surfactant (a) present in the final composition is greater than the amount of the amphoteric surfactant (b); and
   wherein the ratio of nonionic surfactant (a) to anionic surfactant (c) is at least about 1.9:1, by weight, based on the weight percent of each surfactant in the final composition.

2. The composition of claim 1 wherein the at least one nonionic surfactant (a) is present in the composition in an amount of from about 7% to about 10%, by weight, based on the total of weight of the composition.

3. The composition of claim 2 wherein the non-ionic surfactant is selected from lauryl glucoside, decyl glucoside, coco glucoside, and mixtures thereof.

4. The composition of claim 1 wherein the amphoteric surfactant (b) is present in the composition in an amount of from about 4% to about 8%, by weight, based on the total of weight of the composition.

5. The composition of claim 4 wherein the at least one amphoteric surfactant (b) is selected from coco betaine, cocoamidopropyl betaine, behenyl betaine, capryl/capramidopropyl betaine, lauryl betaine, and mixtures thereof.

6. The composition of claim 1 wherein the at least one anionic surfactant (c) is selected from salts of each of alkyl sulfates, alkyl ether sulfates, acyl isethionates, acyl glycianates, acyl taurates, acyl amino acids, acyl sarcosinates, sulfosuccinates, sulfonates, wherein the alkyl and acyl groups of these compounds comprise from 6 to 24 carbon atoms.

7. The composition of claim 6 wherein the anionic surfactant (c) is present in the composition in an amount of from about 2.5% to about 5%, by weight, based on the total of weight of the composition.

8. The composition of claim 1, wherein the at least one anionic surfactant (c) is selected from sodium lauryl sulfate, sodium laureth sulfate, sodium cocoyl isethionate, sodium lauroyl methyl isethionate, sodium cocoyl taurate, sodium methyl cocoyl taurate, sodium cocoyl glycinate, potassium cocoyl glycinate, disodium laurel sulfosuccinate, sodium C14-16 olefin sulfonate, and mixtures thereof.

9. The composition of claim 1, wherein the cationic silane or cationic silane oligomer (d) is present in the composition in an amount of from about 0.1% to about 3% by weight, based on the total of weight of the composition.

10. The composition of claim 9 wherein the cationic silane or cationic silane oligomer (d) is selected from 3-mercaptopropyltriethoxysilane, aminoalkyltrialkoxysilanes, oligomers thereof, and mixtures thereof.

11. The composition of claim 10 wherein the aminoalkyltrialkoxysilane is selected from 3-aminopropyltriethoxysilane, oligomers thereof, and mixtures thereof.

12. The composition of claim 9 further comprising one or more component selected from a pH adjusting agent, a preservative, an antioxidant, a fragrance, a chelating agent, a colorant, and mixtures thereof.

13. The composition of claim 1 having a viscosity from about 4000 cPs to about 6000 cPs.

14. The composition of claim 1 having a pH from about 8 to about 4.5.

15. An aqueous cleaning and conditioning composition comprising:
   (a) from about 6% to about 20% of at least one nonionic surfactant selected from lauryl glucoside, decyl glucoside, and mixtures thereof;
   (b) from about 3% to about 10% of at least one amphoteric surfactant selected from cocoamphopropionate, cocoamidopropyl betaine, and mixtures thereof;
   (c) from about 2% to about 8% of at least one anionic surfactant selected from sodium cocoyl taurate, sodium cocoyl glycinate, sodium cocoyl taurate, and sodium laureth sulfate, and mixtures thereof; and
   (d) from about 0.01% to about 5% of at least one cationic silane, cationic silane oligomer, or a mixture thereof selected from the group consisting of an alkoxysilane, and oligomer of the alkoxysilane, and mixtures thereof;
   wherein the amount of nonionic surfactant (a) present in the final composition is greater than the amount of the amphoteric surfactant (b), and the ratio of nonionic surfactant (a) to anionic surfactant (c) is from about 1.9:1 to about 5:1, based on the weight percent of each surfactant in the final composition.

16. The composition of claim 15 wherein the silane is 3-aminopropyltriethoxysilane, oligomers thereof, and mixtures thereof.

17. A method of cleansing and conditioning hair comprising contacting the hair with an aqueous cleansing composition according to claim 1.

18. A method of conditioning a keratinous substrate involving contacting the keratinous substrate with the composition of claim 15.

19. A method of increasing the deposition of non-ionic silicone polymers onto a keratinous substrate involving contacting the keratinous substrate with a non-ionic silicone polymer and the composition of claim 15.

20. A method of increasing the deposition of hydrophobic non-ionic conditioning agents onto a keratinous substrate comprising contacting the keratinous substrate with a non-ionic conditioning agent and the composition of claim 15.

* * * * *